(12) United States Patent
Marn

(10) Patent No.: US 7,092,492 B2
(45) Date of Patent: Aug. 15, 2006

(54) UNIVERSAL RADIOLOGIC PATIENT POSITIONING MARKER

(75) Inventor: Charles Marn, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/996,637

(22) Filed: Nov. 24, 2004

(65) Prior Publication Data

US 2005/0157847 A1    Jul. 21, 2005

Related U.S. Application Data

(60) Provisional application No. 60/524,655, filed on Nov. 24, 2003.

(51) Int. Cl.
*A61B 19/00* (2006.01)
*G09F 7/00* (2006.01)

(52) U.S. Cl. .................. 378/165; 378/162; 378/205

(58) Field of Classification Search ............... 378/162, 378/163, 165, 177, 179, 205, 20
See application file for complete search history.

(56) References Cited

U.S. PATENT DOCUMENTS

| 2,433,480 | A |   | 12/1947 | Rendich |
|---|---|---|---|---|
| 2,649,548 | A | * | 8/1953 | Greenberg ................. 378/165 |
| 4,058,733 | A |   | 11/1977 | Stembel |
| 4,127,774 | A | * | 11/1978 | Gillen ........................ 378/165 |
| 4,267,641 | A |   | 5/1981 | Shinozaki et al. |
| 4,274,006 | A | * | 6/1981 | Caine ........................ 378/165 |
| 4,426,723 | A |   | 1/1984 | Rouse |
| 4,429,412 | A |   | 1/1984 | Pierce et al. |
| 4,698,836 | A |   | 10/1987 | Minasian |
| 4,744,100 | A | * | 5/1988 | Bauer et al. ................ 378/187 |
| 5,149,965 | A | * | 9/1992 | Marks ..................... 250/252.1 |
| 5,224,147 | A |   | 6/1993 | Collin et al. |
| 5,640,438 | A |   | 6/1997 | Talluto et al. |
| 6,459,772 | B1 | * | 10/2002 | Wiedenhoefer et al. .... 378/163 |

\* cited by examiner

*Primary Examiner*—Edward J. Glick
*Assistant Examiner*—Krystyna Suchecki
(74) *Attorney, Agent, or Firm*—Medlen & Carroll, LLP

(57) ABSTRACT

The present invention relates to autoradiographic marking devices. In particular, the present invention provides compositions useful for marking X-ray films.

8 Claims, 3 Drawing Sheets

Signature Shadows

UNIVERSAL RADIOLOGIC PATIENT POSITIONING MARKER

This application claims priority to U.S. Provisional Patent Application Ser. No. 60/524,655, filed Nov. 24, 2003, incorporated herein by reference in its entirety.

FIELD OF THE INVENTION

The present invention relates to autoradiographic marking devices. In particular, the present invention provides compositions useful for marking X-ray films.

BACKGROUND OF THE INVENTION

Proper examination of X-ray films requires specific knowledge regarding the orientation of the X-ray film and the patient during exposure to an X-ray source. Certain patient positioning information is frequently embedded in radiographic images by placing a radio-opaque marker on the film or cassette prior to exposure. Two of the most common annotations are sidedness (e.g., left or right) and patient position (e.g., upright, supine, or decubitus). Gathering this type of information enables the proper analysis of X-ray films. For example, knowledge of the proper alignment of a patient in an upright position becomes critical for the detection of small amounts of free intra-abdominal air, an important indicator of gastrointestinal perforation.

X-ray opaque markers have been used for decades to permanently attach patient information to X-ray images. However, currently available X-ray opaque markers are deficient in multiple regards. For example, a commonly used position marker uses three tiny metal balls inside a small plastic globe. When exposed in the upright position, the balls fall to the bottom of the sphere. When exposed in the supine position, the balls are in the center of the sphere. However, this device does a poor job at communicating the range of positions from upright to supine, for example, because the ball movement is often inconsistent. Furthermore, this device describes only the position of the cassette and tells nothing of the relationship of the X-ray beam to the cassette. This device is also subject to damage and distortion of the outer plastic globe leading to poor mobility of the balls and a distorted characterization of position.

Other commercially available markers usually involve the assembly of individual letters onto a letter mount. These markers are costly to produce as they require the production of many individual pieces, and are time consuming to use because the letters or numbers or other indicia must be individually set up for each use. The most common markers are the two-piece, left and right marker that may include the technician's name or number. These markers are individually and temporarily secured to the film cassette when in use by tape. This requires the technician to carry messy tape and often results in the loss of the small markers. These markers provide no information regarding patient position at the time the X-ray is taken.

What is needed is a marker which more accurately describes the orientation of the cassette in relation to the X-ray beam, thereby effectively communicating patient position throughout the range of upright to supine, and which is durable and not prone to damage.

SUMMARY OF THE INVENTION

The present invention relates to autoradiographic marking devices. In particular, the present invention provides compositions useful for marking X-ray films.

Accordingly, in some embodiments, the present invention provides a composition comprising a radiologic patient positioning marker, wherein the radiologic patient positioning marker comprises at least one X-ray opaque fluid filled object and a 3-dimensional X-ray opaque orientation object. In some embodiments, the at least one X-ray opaque fluid filled object and the 3-dimensional X-ray opaque orientation object are located in a fixed position within a housing device formed of material transparent to X-ray radiation. The present invention is not limited to a particular material transparent to X-ray radiation. Indeed, a variety of materials are contemplated including, but not limited to, plastic and other composite materials. Likewise, the present invention is not limited to a particular shape for the housing device. Indeed, a variety of shapes are contemplated including, but not limited to a rectangle, square, polygon, triangle and sphere.

In some embodiments, the 3-dimensional X-ray opaque orientation object produces a signature shadow on radiographic film when exposed to X-ray radiation from one direction and a different signature shadow on radiographic film when exposed to X-ray radiation from an alternate direction. In still further embodiments, the 3-dimensional X-ray opaque orientation object produces a signature shadow on radiographic film when exposed to X-ray radiation from one direction, a second signature shadow on radiographic film when exposed to X-ray radiation from a second direction, and a third signature shadow on radiographic film when exposed to X-ray radiation from a third direction.

The present invention also provides a kit comprising a radiologic patient positioning marker and a means of removably attaching the radiologic patient-positioning marker to a radiographic film cassette. In some embodiments, the means of attaching the radiologic patient-positioning marker comprises the use of Velcro strips. In other embodiments, magnets are used for removably attaching the radiologic patient-positioning marker to the radiographic film cassette. In still further embodiments, an integrated locking system is used. In some embodiments, the locking system prevents the radiographic film cassette from acquiring a film unless the radiologic patient-positioning marker is properly installed. In other embodiments, the device may simply lay next to the patient held in place by gravity on an X-ray table for a supine image or attached to a vertical cassette holder when an upright film is obtained.

DEFINITIONS

The term "3-dimensional X-ray opaque orientation object" refers to an object made of X-ray opaque material that resides within an X-ray transparent housing unit. The 3-dimensional X-ray opaque orientation object may be in the form of letters (e.g., R, L, S, O, A and P for right, left, sinister, occipital, anterior, and posterior, respectfully) or other shapes, such that some aspect of X, Y, and Z coordinates can be differentiated if images are taken in a plurality of views. The 3-dimensional X-ray opaque orientation object, when used as discussed in the present invention, shields radiographic film from exposure to an X-ray source, thereby casting a "signature shadow" onto X-ray film. After the X-ray film is developed, the shadow can be analyzed to determine the orientation of the film with respect to patient position.

The term "signature shadow" refers to one of any number of shadows cast by the radiologic patient-positioning marker dependent upon both the direction from which the X-ray source passes through the radiologic patient positioning marker and the orientation of the radiologic patient-positioning marker upon the radiographic film cassette. For example, the signature shadow cast by a radiologic patient positioning marker in one embodiment of the present invention, when the marker is used in the upright position and exposed to an X-ray source from a particular direction (A) is shown in FIG. 3A, whereas the signature shadow cast by the radiologic patient-positioning marker when the marker is used in the upright position and exposed to an X-ray source from a different direction (B) is shown in FIG. 3B.

DETAILED DESCRIPTION OF THE PREFERRED EMBODIMENTS

The present invention relates to autoradiographic marking devices. The present invention provides a composition comprising a radiologic patient positioning marker, wherein the radiologic patient positioning marker comprises at least one X-ray opaque fluid filled object and a 3-dimensional X-ray opaque orientation object. In some embodiments, the at least one X-ray opaque fluid filled object and the 3-dimensional X-ray opaque orientation object are located in a fixed position within a housing device formed of material transparent to X-ray radiation. The present invention is not limited to a particular material transparent to X-ray radiation. Indeed, a variety of materials are contemplated including, but not limited to, plastic and other composite materials. Likewise, the present invention is not limited to a particular shape for the housing device. Indeed, a variety of shapes are contemplated including, but not limited to a rectangle, square, polygon, triangle and sphere. The following description of the invention is provided for illustrative purposes and should not be construed as limiting the scope of the invention as set forth in the claims.

Figure 1:
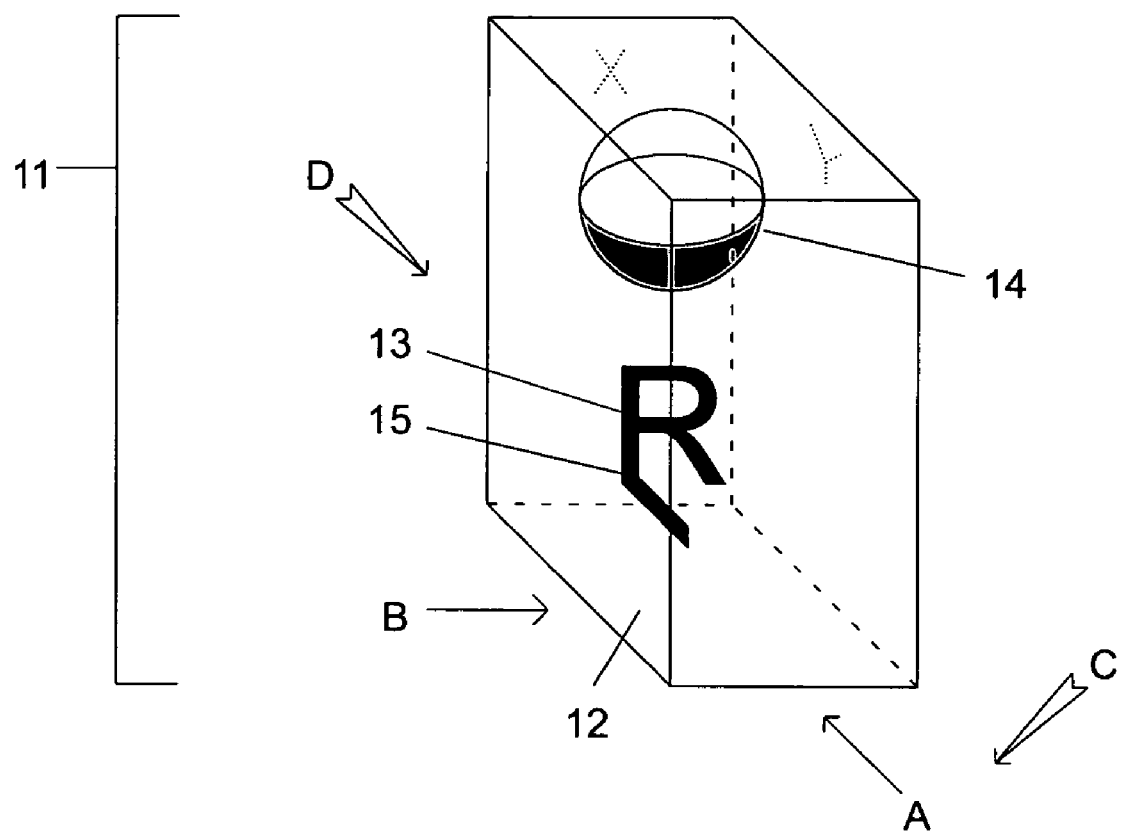
FIG. 1 illustrates a marker device in one embodiment of the present invention.
Figure 2A:
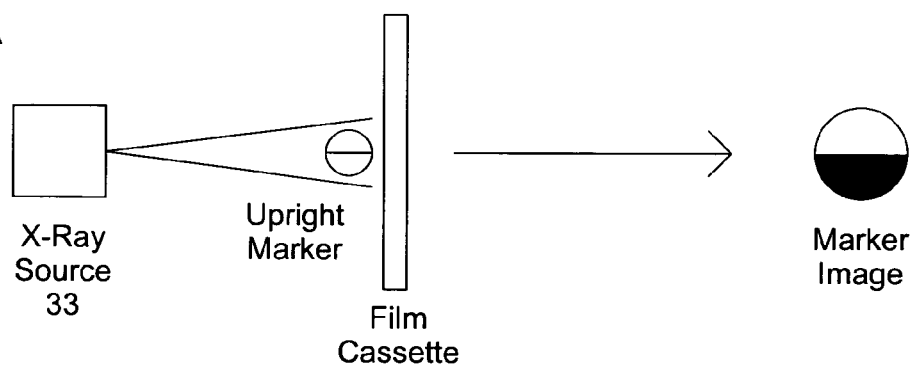
FIG. 2 shows various illustrative combinations of positions in which the radio-opaque fluid filled sphere portion of a radiologic patient positioning marker and a radiographic film cassette may be exposed to an X-ray source. The signature shadow cast upon X-ray film by the radio-opaque fluid filled sphere from different angles of exposure is depicted. 2A (upright marker); 2B (supine marker); and 2C (marker at 45 degree angle to X-ray source).
Figure 2B:
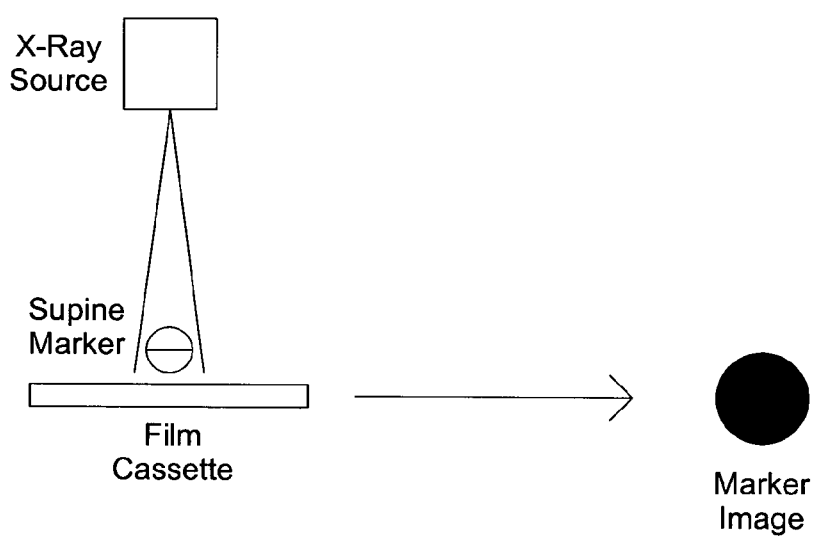
Figure 2C:
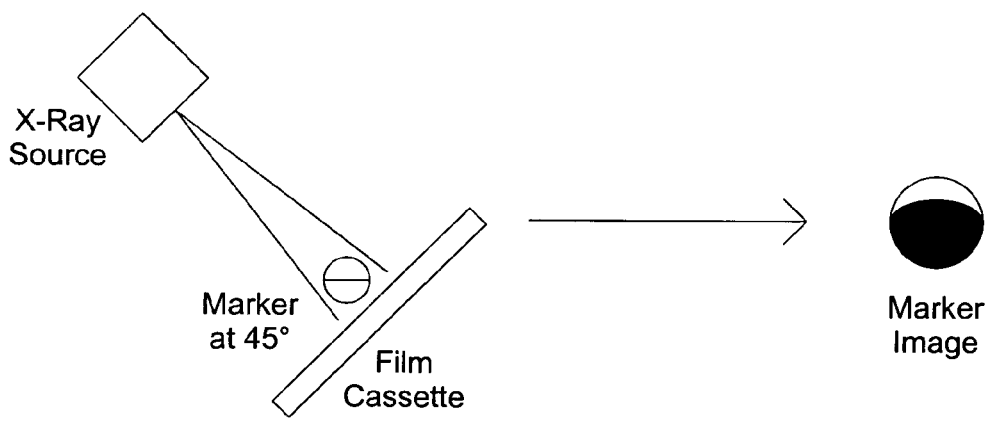
Figure 3:
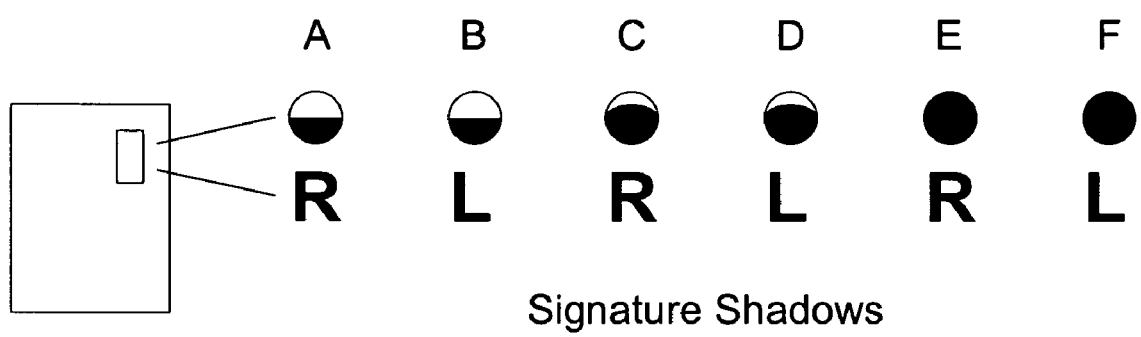
FIG. 3A depicts the signature shadow cast from the marker onto radiographic film when used in an upright position and exposed to an X-ray source from direction A in FIG. 1.
FIG. 3B depicts the signature shadow cast from the marker onto radiographic film when used in an upright position and exposed to an X-ray source from direction B in FIG. 1.
FIG. 3C depicts the signature shadow cast from the marker onto radiographic film when used in an upright position and exposed to an X-ray source from direction C in FIG. 1.
FIG. 3D depicts the signature shadow cast from the marker onto radiographic film when used in an upright position and exposed to an X-ray source from direction D in FIG. 1.
FIG. 3E depicts the signature shadow cast from the marker onto radiographic film when used in a supine position and exposed to an X-ray source from direction A in FIG. 1.
FIG. 3F depicts the signature shadow cast from the marker onto radiographic film when used in a supine position and exposed to an X-ray source from direction B in FIG. 1.

A preferred form of the radiologic patient-positioning marker 11 as shown in FIGS. 1–3, includes an X-ray transparent housing device 12 containing an X-ray opaque 3-dimensional orientation object 13, and an X-ray opaque fluid-filled object 14. In some embodiments, the radiologic patient positioning marker 11 comprises at least one X-ray opaque fluid filled object 14 and a 3-dimensional X-ray opaque orientation object 13, both of which are located, for example, in a fixed position within a housing device 12 formed of material transparent to X-ray radiation. In one preferred embodiment, a rectangular X-ray transparent housing device 12 houses one partially filled, X-ray opaque fluid filled sphere 14, and X-ray opaque three-dimensional block letters (R and L) 13 which share a common vertical axis 15, both of which are located in a fixed position within the housing device (FIG. 1).

Although the invention has been described with specific reference to a positioning marker housing a 3-dimensional orientation object that is capable of forming either a "L" or a "R" on radiographic film, it will be recognized that the principle is applicable to other combinations of two or more characters, shapes, or other designations that represent the orientation of the film with respect to the subject, cassette, or equipment. For example, a single X-ray opaque 3-dimensional orientation object composed to form two different letters could form both a "S" and an "O" (abbreviations used for "sinister" and "occipital") on radiographic film depending upon the orientation of the radiologic patient positioning marker and the direction of exposure to the X-ray source. Similarly, a single X-ray opaque 3-dimensional orientation object could form both an "A" and a "P" (abbreviations for "anterior" and "posterior") on radiographic film depending upon the orientation of the radiologic patient positioning marker and the direction of exposure to the X-ray source.

In an upright position (FIG. 2a), when the positioning marker 11 is exposed to an X-ray source 33 from one direction (e.g., direction A in FIG. 1), the X-ray opaque fluid filled sphere 14 and the X-ray opaque 3-dimensional block letters 13 cast one type of signature shadow on the radiographic film (FIG. 3a). When the positioning marker 11 is exposed to an X-ray source 33 from a second direction (e.g., direction B in FIG. 1), the X-ray opaque fluid filled sphere 14 and the X-ray opaque 3-dimensional block letters 13 cast a second type of signature shadow on the radiographic film (FIG. 3b). When the positioning marker 11 is exposed to an X-ray source 33 from yet a third direction (e.g., direction C in FIG. 1, FIG. 2C, marker at 45 degree angle from X-ray source 33), the X-ray opaque fluid filled sphere 14 and the X-ray opaque 3-dimensional block letters 13 cast a third type of signature shadow on the radiographic film (FIG. 3c). When the positioning marker 11 is exposed to an X-ray source 33 from a fourth direction (e.g., direction D in FIG. 1, FIG. 2C, marker at 45 degree angle from X-ray source 33), the X-ray opaque fluid filled sphere 14 and the X-ray opaque 3-dimensional block letters 13 cast a fourth type of signature shadow on the radiographic film (FIG. 3d).

When the positioning marker 11 is used in a supine position (FIG. 2B), one of two signature shadows will appear on the radiographic film. If the marker 11 is placed on the cassette or the film such that side X (See FIG. 1) is flat against the cassette or film (meaning that the marker will be exposed to an X-ray source from direction A of FIG. 1.), the signature shadow of FIG. 3e will be cast onto the radiographic film. If the marker is placed on the cassette or the film such that side Y (See FIG. 1) is flat against the cassette or film (meaning that the marker will be exposed to an X-ray source from direction B of FIG. 1), the signature shadow of FIG. 3f will be cast onto the radiographic film.

The radiologic patient-positioning marker 11 can be used anytime an X-ray is taken. In some embodiments, after X-ray film is placed into a radiographic cassette in the conventional manner, the radiologic patient positioning marker 11 can be placed on the flat surface of the cassette in a desired location, such as in the lower right hand corner. In some embodiments, a kit containing the radiologic patient positioning marker and Velcro strips are used to attach the radiologic patient-positioning marker 11 to a radiographic cassette. In other embodiments, a kit containing the radiologic patient positioning marker 11 and magnets are used to attach the radiologic patient-positioning marker 11 to a radiographic cassette. In still other embodiments, the placing of X-ray film into the cassette is dependent upon an integrated locking system between the radiologic patient-positioning marker 11 and the radiographic cassette.

The radiographic cassette can then be used in the normal fashion. That is, the cassette can be placed in alignment with a patient, or portion thereof, to be X-rayed and a source of X-rays so that the shadow of the radiologic patient positioning marker 11 and that of the patient will fall on the X-ray film. When the film has been thusly exposed to X-rays and properly developed, not only will the shadow of the patient, or portion thereof, X-rayed be visible on the film, but the shadow of the X-ray opaque portions of the radiologic patient positioning marker 11 will also be visible. Specifically, shadows from the X-ray opaque 3-dimensional orientation object 13 and the X-ray opaque fluid filled object 14 will be visible.

The image created by the radiologic patient positioning marker 11 on a developed film is shown, as described above, in FIGS. 1–3. Those skilled in the art, of course, will understand the importance in reading X-ray film negatives of having a positive, automatic indication (not subject to operator error) of whether the film was flat or whether the film was vertical during irradiation and, in the latter case, which direction is up. Furthermore, the combined use of the X-ray opaque 3-dimensional orientation object 13 and the X-ray opaque fluid filled object 14 permits an accurate description of the orientation of the film in relation to the X-ray source, thereby effectively communicating patient position throughout the range of upright to supine.

When the X-ray has been exposed, the X-ray marker 11 can be removed from the surface of the radiographic cassette. Removal can be accomplished by grasping the positioning marker and pulling sufficiently strongly to overcome the Velcro, magnetic, or other attachment. In other embodiments, the film is removed from the cassette when the integrated locking system between the radiologic patient positioning marker 11 and the radiographic cassette is released.

In view of the foregoing, it should be apparent that the present invention now provides an improved patient positioning marker assembly that is useful in enabling proper marking to be accomplished in a variety of radiographic procedures. Although X-ray radiation is discussed in the foregoing disclosure, it will be understood that the marker of the present invention is suitable for use with other exposure systems and associated radiation or other energy sources. It will only be necessary to select materials that are opaque and transparent to the particular radiation or other exposing source that is being used.

For example, the present invention is applicable to digital technology. While the markers have been presented for traditional applications in a file cassette environment, the present invention includes the same identification tasks applied to new and emerging methods of plain radiographic imaging such as Computer Radiography and Direct Capture Radiography. For example, in some embodiments, the radiographic patient position marker is attached to the cassette for phosphor plate digital imaging, or to the housing of the Direct Capture receiver.

Having described the invention in detail, those skilled in the art will appreciate that various modifications, alterations, and changes of the invention may be made without departing from the spirit and scope of the present invention. Therefore, it is not intended that the scope of the invention be limited to the specific embodiments illustrated and described.

What is claimed is:

1. A composition comprising a radiologic patient-positioning marker, wherein said radiologic patient positioning marker comprises:
    at least one X-ray opaque fluid filled object, wherein said X-ray opaque fluid filled object is configured to cast a signature shadow, wherein said signature shadow represents the relationship between a film cassette and X-ray source throughout a patient position range of upright to supine; and
    a 3-dimensional X-ray opaque orientation object, wherein said 3-dimensional X-ray opaque orientation object comprises 3-dimensional block letters that share a common vertical axis but do not share a common horizontal axis.

2. The composition of claim 1, wherein said at least one X-ray opaque fluid filled object and said 3-dimensional X-ray opaque orientation object are located in a fixed position within a housing device formed of material transparent to X-ray radiation.

3. The composition of claim 2, wherein said housing device is formed of plastic or other composite materials.

4. The composition of claim 2, wherein said housing device is formed in the shape of a rectangle, square, polygon, triangle or sphere.

5. The composition of claim 1, wherein said 3-dimensional X-ray opaque orientation object produces a signature shadow on radiographic film when exposed to X-ray radiation from one direction and a different signature shadow on radiographic film when exposed to X-ray radiation from an alternate direction.

6. The composition of claim 1, wherein said 3-dimensional X-ray opaque orientation object produces a signature shadow on radiographic film when exposed to X-ray radiation from one direction, a second signature shadow on radiographic film when exposed to X-ray radiation from an second direction, and a third signature shadow on radiographic film when exposed to X-ray radiation from a third direction.

7. A kit comprising:
    the composition of claim 1; and
    a means of removably attaching said radiologic patient positioning marker to a radiographic film cassette.

8. The kit of claim 7, wherein said means of removably attaching said radiologic patient positioning marker comprises Velcro strips or magnets.

* * * * *